(12) United States Patent  (10) Patent No.: US 7,238,816 B2
Puentener et al.  (45) Date of Patent: Jul. 3, 2007

(54) PREPARATION OF EPOTHILONE DERIVATIVES

(75) Inventors: Kurt Puentener, Basel (CH); Michelangelo Scalone, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/400,682

(22) Filed: Apr. 7, 2006

(65) Prior Publication Data

US 2006/0241156 A1  Oct. 26, 2006

(30) Foreign Application Priority Data

Apr. 21, 2005 (EP) .................. 05103218

(51) Int. Cl.
*C07D 313/00* (2006.01)
(52) U.S. Cl. ........................ 549/271
(58) Field of Classification Search ............ 549/271
See application file for complete search history.

(56) References Cited

U.S. PATENT DOCUMENTS

2004/0053910 A1  3/2004  Danishefsky et al.

FOREIGN PATENT DOCUMENTS

WO    WO 2004/018478    3/2004

OTHER PUBLICATIONS

Danishefsky et al., *J. Am. Chem. Soc.*, 125, pp. 2899-2901 (2003).
Nolan et al., *Organometallics*, 18, pp. 5416-5419 (1999).
Mol, J.C., *Adv. Synth. Catal.*, 344, pp. 671-677 (2002).
Fuerstner, A. et al, *J. Org. Chem.*, vol. 65:7, (2000) pp. 2204-2207 XP002395456.

*Primary Examiner*—Kamal A. Saeed
*Assistant Examiner*—Karen Cheng
(74) *Attorney, Agent, or Firm*—George W. Johnston; Dennis P. Tramaloni; Brian C. Remy

(57) ABSTRACT

The invention comprises a novel process for the preparation of an epothilone derivative of formula I:

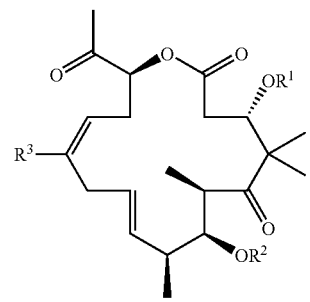

wherein $R^1$ and $R^2$ independently from each other represent hydrogen or protecting groups and $R^3$ is methyl or trifluoromethyl, which are useful precursors in the synthesis of the desoxyepothilone derivatives of the formula IV:

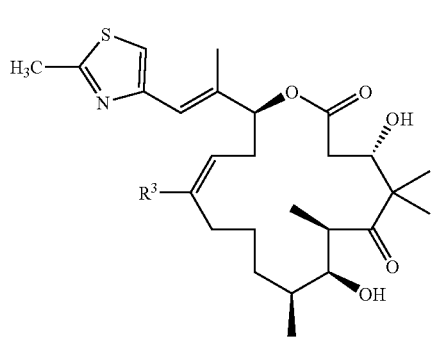

wherein $R^3$ is methyl or trifluoromethyl.

The desoxepothilones of formula IV inhibit the growth of tumor cells and are therefore promising candidates for novel anticancer agents.

7 Claims, No Drawings

ffff

PREPARATION OF EPOTHILONE DERIVATIVES

PRIORITY TO RELATED APPLICATIONS

This application claims the benefit of European Application No. 05103218.3, filed Apr. 21, 2005, which is hereby incorporated by reference in its entirety.

FIELD OF THE INVENTION

The present invention is concerned with a novel process for the preparation of epothilone derivatives which can be used for the preparation of 9,10-dehydro-12,13-desoxyepothilone derivatives.

BACKGROUND OF THE INVENTION 9,10-dehydro-12,13-desoxyepothilone derivatives of the formula IV:

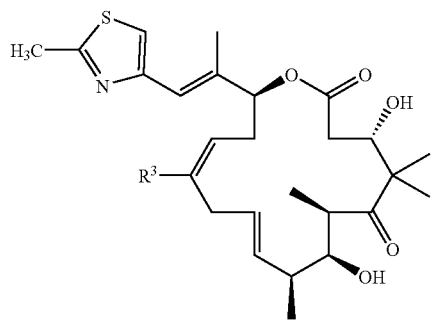

IV wherein R³ is methyl or trifluoromethyl, inhibit the growth of tumor cells and are therefore promising candidates for novel anticancer agents (see Danishefsky et al., *J. Am. Chem. Soc.* 2003, 125, 2899–2901; and International Patent Application Publication No. WO 2004/018478 A2).

The same authors (Danishefsky et al.) report a process for the preparation of epothilone derivatives which is described in scheme 1 below.

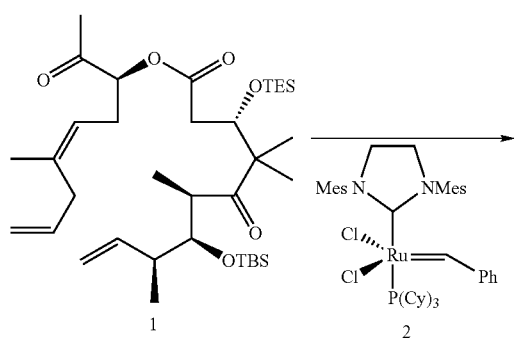

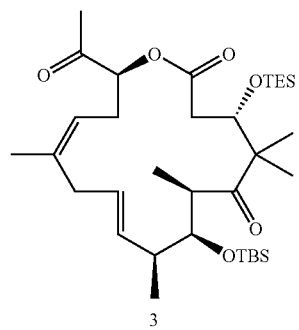

TES = triethyl silyl
TBS = tert. butyl dimethyl silyl
MES = 2,4,6-trimethylphenyl
Ph = phenyl
Cy = cyclohexyl According to this process an olefin-precursor of formula 1 is converted in the presence of a Grubbs II catalyst of formula 2 to the respective epothilone derivative of formula 3 in a yield of 78%.

In the attempt to find an alternative synthesis which is feasible on a technical scale the objective of the present invention was to further improve the selectivity and the yield of the cyclization process.

It was found that with the process of the present invention, as outlined below, this improvement could surprisingly be achieved.

SUMMARY OF THE INVENTION

The present invention relates to a novel process for the preparation of an epothilone derivative of formula I:

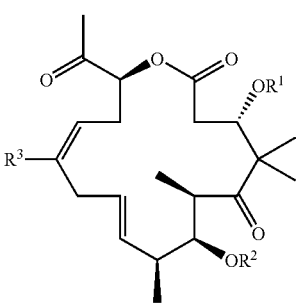

I wherein:
R¹ is hydrogen or a protecting group;
R² is hydrogen or a protecting group; and
R³ is methyl or trifluoromethyl;

comprising reacting an olefin-precursor compound of formula II:

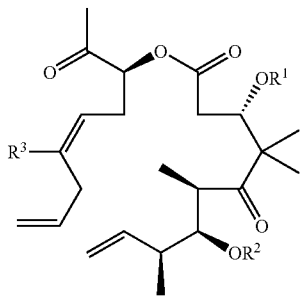

wherein $R^1$, $R^2$ and $R^3$ are defined above, in the presence of an organic solvent and a Ruthenium catalyst of formula III:

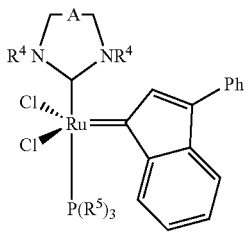

wherein:
A is a single or a double bond,
$R^4$ is phenyl optionally substituted by one to five lower alkyl groups, and
$R^5$ is cyclohexyl or phenyl.

The epothilone derivatives of formula I can be used for the preparation of 9,10-dehydro-12,13-desoxyepothilone derivatives of the formula IV:

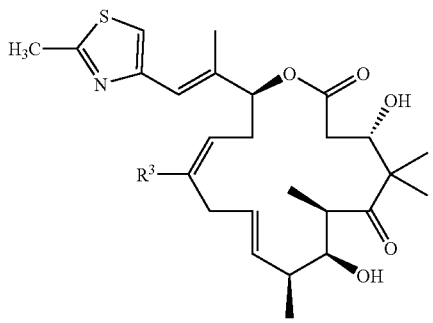

wherein $R^3$ is methyl or trifluoromethyl.

DETAILED DESCRIPTION OF THE INVENTION

Unless otherwise indicated, the following definitions are set forth to illustrate and define the meaning and scope of the various terms used to describe the invention herein.

The term protecting group as used herein in the context of $R^1$ and $R^2$ means a hydroxy protecting group. Suitable hydroxy protecting groups are: (a) tri lower alkyl silyl groups selected from the group consisting of trimethyl silyl (TMS), triethyl silyl (TES), tert-butyl dimethyl silyl (TBS), triisopropyl silyl (TIPS), tert-butyl diphenyl silyl (TBDPS), and diethyl isopropyl silyl (DEIPS), preferably triethyl silyl (TES) and tert-butyl dimethyl silyl (TBS); (b) alkoxyalkyl groups selected from the group consisting of methoxymethyl (MOM), (2-methoxyethoxy)methyl (MEM), benzyloxymethyl (BOM) and beta-(trimethylsilyl)-ethoxymethyl (SEM); or (c) acyl groups selected from the group consisting of acetyl (Ac), α-chloroacetyl and benzoyl (Bz).

Preferred hydroxy protecting groups are tri lower alkyl silyl groups selected from the group consisting of trimethyl silyl (TMS), triethyl silyl (TES), tert-butyl dimethyl silyl (TBS), triisopropyl silyl (TIPS), tert-butyl diphenyl silyl (TBDPS), and diethyl isopropyl silyl (DEIPS), with triethyl silyl (TES) and tert-butyl dimethyl silyl (TBS) being especially preferred.

The term "lower alkyl", alone or in combination with other groups, refers to a branched or straight-chain monovalent alkyl radical of one to six carbon atoms, and in preferred embodiments the lower alkyl one to four carbon atoms. Examples of lower alkyls include methyl, ethyl, n-propyl, isopropyl, n-butyl, s-butyl, isobutyl, t-butyl, n-pentyl, 3-methylbutyl, n-hexyl, 2-ethylbutyl and the like.

The process of the present invention comprises the cyclization of an olefin-precursor of the formula II:

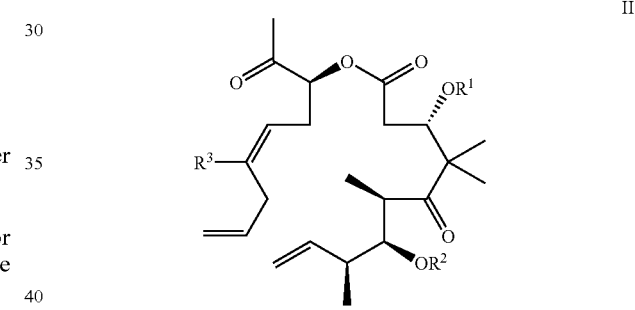

wherein:
$R^1$ is hydrogen or a protecting group;
$R^2$ is hydrogen or a protecting group; and
$R^3$ is methyl or trifluoromethyl;

in the presence of an organic solvent and a Ruthenium (Ru) catalyst of the formula III:

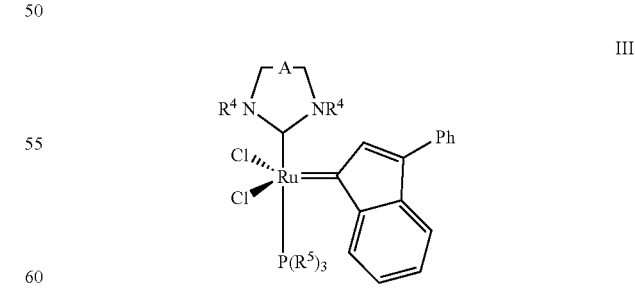

wherein:
A is a single or a double bond,
$R^4$ is phenyl optionally substituted by one to five lower alkyl groups, and
$R^5$ is cyclohexyl or phenyl.

This cyclization reaction which is known as "ring closing metathesis" reaction can preferably be performed with a Ruthenium catalyst of formula III, wherein A is a single or a double bond, $R^4$ is 2,4,6-trimethylphenyl or 2,6-diisopropylphenyl, and $R^5$ is cyclohexyl or phenyl.

In a preferred embodiment, A is a double bond. In another referred embodiment A is a double bond, $R^4$ is 2,4,6-trimethylphenyl and $R^5$ is cyclohexyl. In another referred embodiment A is a double bond, $R^4$ is 2,4,6-trimethylphenyl and $R^5$ is phenyl. In another referred embodiment A is a single bond, $R^4$ is 2,4,6-trimethylphenyl and $R^5$ is cyclohexyl. In another referred embodiment A is a double bond, $R^4$ is 2,6-diisopropylphenyl and $R^5$ is cyclohexyl.

Most preferably, the cyclization is performed in the presence of a Ruthenium catalyst of formula III wherein A signifies a double bond, $R^4$ is 2,4,6-trimethylphenyl and $R^5$ is cyclohexyl; or the cyclization is performed in the presence of a Ruthenium catalyst of formula III wherein A signifies a single bond, $R^4$ is 2,4,6-trimethylphenyl and $R^5$ is cyclohexyl.

The reaction conditions used are conditions that a person skilled in the art would commonly apply for ring closure metathesis reactions.

For example, the reaction is preferably performed in a suitable organic solvent wherein said solvent is selected from the group consisting of toluene, methylene chloride, benzene and mesitylene. In a preferred embodiment the organic solvent is toluene.

The reaction temperature is preferably selected in the range of 20° C. and 165° C., more preferably in the range of 80° C. and 120° C., and most preferably in the range of 100° C. and 110° C.

The amount of catalyst used in the process of the present invention is preferably in the range of 0.1 to 15 mol % relative to substrate, more preferably in the range of 1 to 5 mol % relative to substrate.

Preferably, the reaction can also be carried out in the form of a "double addition" process, meaning that a solution of the substrate and a solution of the catalyst are simultaneously added within 100 minutes with the aid of syringe pumps to the boiling solvent (substrate concentration after complete addition=10 mM).

The olefin-precursor of formula I can be prepared according to Danishefsky et al., *J. Am. Chem. Soc.* 2003, 125, 2899–2901 or U.S. Patent Application Publication No. 2004/0053910 A1 by following scheme 2:

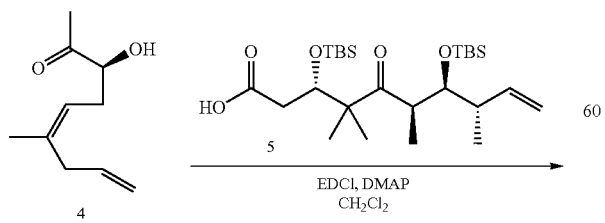

-continued

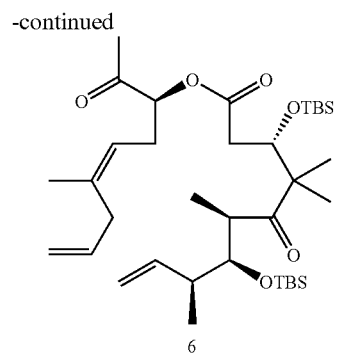

6

TBS = tert. butyl dimethyl silyl
EDCl = 1-(3-dimethylaminopropyl)-3-ethyl-carbodiimide. HCl
DMAP = Dimethylaminopyridine The Ruthenium catalysts of formula III can be prepared according to S. P. Nolan, *Organometallics* 1999, 18, 5416–5419, by following scheme 3:

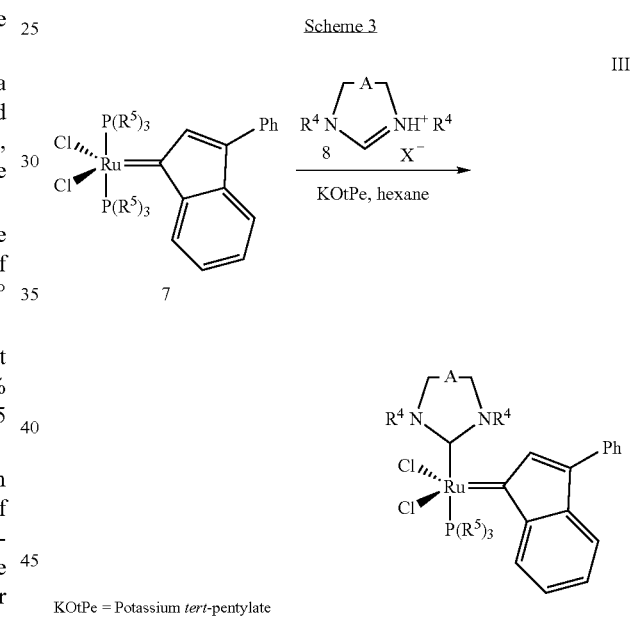

KOtPe = Potassium *tert*-pentylate
X⁻ = Cl⁻ or BF₄⁻

Furthermore, the present invention relates to the use of the process as defined herein before for the preparation of desoxyepothilone derivatives of the formula IV:

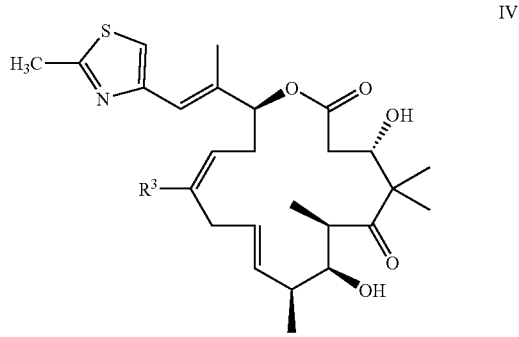

wherein $R^3$ is methyl or trifluoromethyl.

This can be accomplished, for example, according to U.S. Patent Application Publication No. 2004/0053910 A1 by following scheme 4 via the introduction of the thiazole moiety and the subsequent deprotection or chemical removal of the protecting groups as follows:

Scheme 4

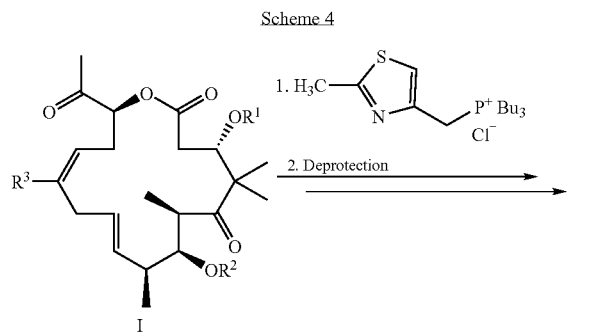

The reaction with the Wittig reagent (Step 1) can be carried out under basic conditions, e.g. by using a base such as n-butyl lithium (N-BuLi) or potassium hexamethyldisilazane (KHMDS) in a polar solvent like tetrahydrofurane in a temperature range from −78° C. up to room temperature.

The deprotection of the protecting groups is carried out under acidic or slightly basic conditions. Preferably, the deprotection is carried out under acidic conditions. For example, silyl ethers can be cleaved by HF in pyridine. Ether groups such as methoxymethyl (MOM) can be cleaved by using concentrated HCl in methanol. In case acyl groups are used as hydroxy protecting groups, slightly basic conditions such as $K_2CO_3$ in aqueous methanol (for acetyl groups) or pyridine (for α-chloroacetyl groups) or NaOH in aqueous methanol (for benzoyl groups) can be applied.

Thus, the present invention relates to the process as defined above, wherein a compound of formula I is converted into a desoxyepothilone derivative of the formula IV:

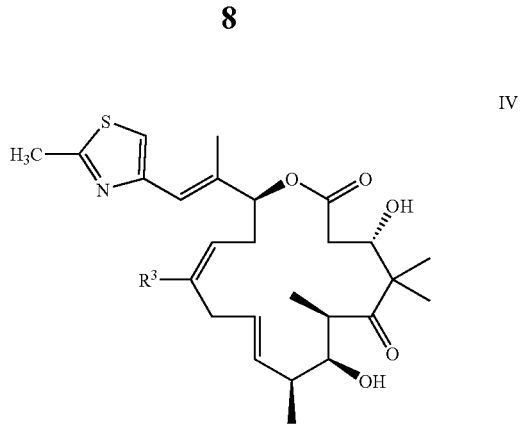

wherein $R^3$ is methyl or trifluoromethyl;

comprising reacting a compound of formula I with a Wittig reagent of the formula V:

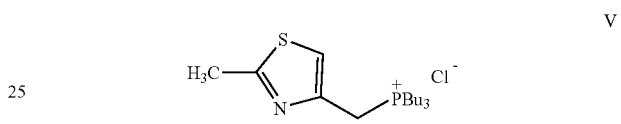

under basic conditions, followed by chemically removing the protecting groups of the resulting product.

Preferably, this process can be used for the preparation of the desoxyepothilone derivative of the formula VI:

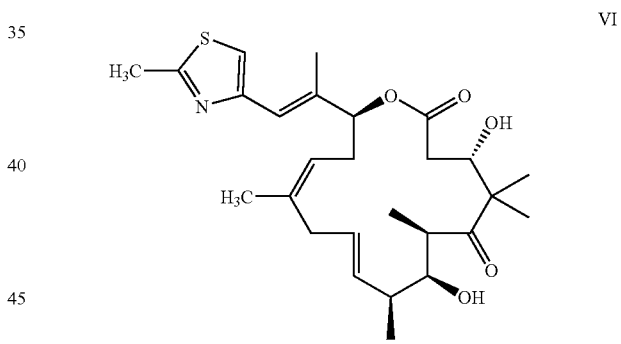

which is 9,10-dehydroepothilone D or 9,10-dehydro-12,13-desoxyepothilone B.

Still in a further embodiment, the present invention relates to the use of the Ruthenium catalyst of formula III:

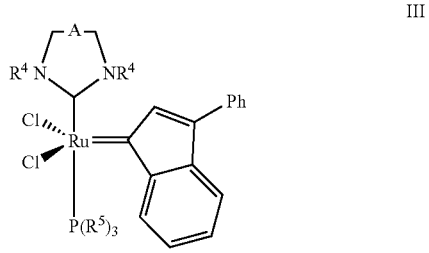

wherein:
A is a single or a double bond,
R⁴ is phenyl optionally substituted by one to five lower alkyl groups, and
R¹ is cyclohexyl or phenyl, for the preparation of epothilone derivatives of the formula I:

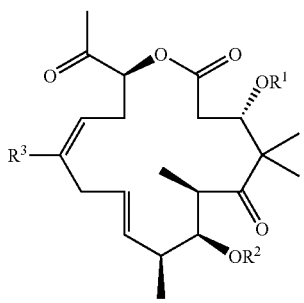

wherein:
$R^1$ is hydrogen or a protecting group;
$R^2$ is hydrogen or a protecting group; and
$R^3$ is methyl or trifluoromethyl.

The desoxyepothilone derivatives of formula IV inhibit the growth of tumor cells and are therefore promising candidates for novel anticancer agents. They especially inhibit the growth of multidrug resistant cancer cell lines. They are preferably useful in treatment of solid tumors. Furthermore, the desoxyepthilone derivatives of formula IV may also be useful for treating and preventing any proliferative disease, autoimmune diseases such as rheumatoid arthritis and infections.

Another embodiment of the present invention is a compound of formula (IV) or a salt or ester thereof made by a process described above.

Another embodiment of the present invention is a compound of formula (IV) or a salt or ester thereof made by a process described above wherein $R^3$ is methyl.

Another embodiment of the present invention is a compound of formula (IV) or a salt or ester thereof made by a process described above wherein $R^3$ is trifluoromethyl.

Another embodiment of the present invention is a compound of formula (I) or a salt or ester thereof made by a process described above.

Another embodiment of the present invention is a compound of formula (I) or a salt or ester thereof made by a process described above wherein $R^1$ is hydrogen.

Another embodiment of the present invention is a compound of formula (I) or a salt or ester thereof made by a process described above wherein $R^1$ is a protecting group.

Another embodiment of the present invention is a compound of formula (I) or a salt or ester thereof made by a process described above wherein $R^2$ is hydrogen.

Another embodiment of the present invention is a compound of formula (I) or a salt or ester thereof made by a process described above wherein $R^2$ is a protecting group.

Another embodiment of the present invention is a compound of formula (I) or a salt or ester thereof made by a process described above wherein $R^3$ is methyl.

Another embodiment of the present invention is a compound of formula (I) or a salt or ester thereof made by a process described above wherein $R^3$ is trifluoromethyl.

Another embodiment of the present invention is a compound of formula (I) or a salt or ester thereof made by a process described above wherein $R^1$ is hydrogen and $R^2$ is hydrogen.

The following examples shall illustrate the invention without further limiting it.

EXAMPLES

Abbreviations
r.t.=room temperature,
ImH₂Mes=1,3-bis-(2,4,6-trimethylphenyl)-2-imidazolidinylidene,
ImMes=1,3-bis-(2,4,6-trimethylphenyl)-2-imidazolylidene,
ImH₂Pr=1,3-bis-(2,6-diisopropylphenyl)-2-imidazolidinylidene,
RCM=ring closing metathesis.

Table of Catalysts Tested

| Catalyst Structure | Chemical Name |
|---|---|
| | [RuCl₂(PCy₃)(ImH₂Mes)(benzylidene)] CAS No. 246047-72-3 |
| | [RuCl₂(PCy₃)(ImH₂Pr)(benzylidene)] CAS No. 373640-75-6 |
| | [RuCl₂(PCy₃)(ImH₂Mes)(3-phenyl-indenylidene)] CAS No. 536724-67-1 |
| | [RuCl₂(PCy₃)(ImMes)(3-phenyl-indenylidene)] CAS No. 254972-49-1 |
| | [RuCl₂(PPh₃)(ImMes)(3-phenyl-indenylidene)] CAS No. 254972-47-9 |

11

Example 1

[RuCl$_2$(PCy$_3$)(ImH$_2$Mes)(3-phenyl-indenylidene)]

A suspension of 383.0 mg (1.08 mmol) of 1,3-bis(2,4,6-trimethylphenyl)-imidazolidinium chloride (commercially available from Aaron Chemistry GmbH, D-85386 Eching) and 0.67 ml (1.14 mmol) of potassium tert.-pentylate (1.7 M in toluene) was suspended in 25 ml hexane and heated at 50° C. for 10 min. A suspension of 500.0 mg (0.54 mmol) of [RuCl$_2$(PCy$_3$)$_2$(3-phenyl-indenylidene)] (commercially available from Umicore AG, D-63457 Hanau-Wolfgang) in 16 ml of hexane was added and the resulting red suspension stirred at 50° C. for 18 h. The reaction mixture was evaporated to dryness and the isolated crude product purified by silica gel chromatography (hexane/diethylether 6:4) to yield 257.0 mg (50%) of the title compound as red crystals. MS: 948.3 (M$^+$). $^{31}$P-NMR (121 MHz, C$_6$D$_6$): 25.8 ppm; $^1$H-NMR (300 MHz, C$_6$D$_6$): 1.00–1.40 (m, 18H); 1.45–1.64 (m, 6H); 1.65–1.95 (m, 6H); 1.80 (s, 3H); 2.23 (s, 6H); 2.38 (s, 3H); 2.85 (s, 3H); 2.87 (s, 3H); 3.10–3.45 (m, 4H); 6.02 (s, 1H); 6.47 (s, 1H); 6.97 (s, 2H); 7.05–7.35 (m, 6H); 7.84 (s, 1H, Ru=CCH); 7.89 (m, 2H); 9.16 (m, 1H). Anal. calcd. for C$_{54}$H$_{69}$N$_2$Cl$_2$PRu: C, 68.34; H, 7.33; N, 2.95. Found: C, 68.61; H, 7.32; N, 2.68.

Example 2

[RuCl$_2$(PCy$_3$)(ImMes)(3-phenyl-indenylidene)]

In analogy to S. P. Nolan, *Organometallics* 1999, 18, 5416–5419, a suspension of 1.55 g (4.33 mmol) of 1,3-bis(2,4,6-trimethylphenyl)-imidazolium chloride (commercially available from Strem Chemicals Inc., D-77672 Kehl) and 2.70 ml (4.59 mmol) of potassium tert.-pentylate (1.7 M in toluene) was suspended in 20 ml hexane and heated at 50° C. for 10 min. 2.00 g (2.17 mmol) of [RuCl$_2$(PCy$_3$)$_2$(3-phenyl-indenylidene)] was added and the resulting red suspension stirred at 50° C. for 15 h. The reaction mixture was allowed to cool to r.t., the formed brown crystals were filtered off and washed with 40 ml pentane. The crystals were dissolved in 30 ml dichloromethane. 30 ml water was added and the organic layer was separated and dried over Na$_2$SO$_4$. The orange solution was evaporated to dryness and the isolated red crystals washed with 30 ml pentane and dried under vacuum to yield 2.05 g (81% yield) of the title compound. MS: 946.3 (M$^+$). $^{31}$P-NMR (121 MHz, C$_6$D$_6$): 27.4 ppm. $^1$H-NMR (300 MHz, C$_6$D$_6$): 1.00–1.40 (m, 18H); 1.47–1.68 (m, 6H); 1.70–1.84 (m, 3H); 1.80 (s, 3H); 1.85–1.95 (m, 3H); 2.04 (s, 3H); 2.20 (s, 3H); 2.24 (s, 3H); 2.45–2.65 (s, 3H); 2.67 (s, 3H); 6.03 (s, 1H); 6.16 (s, 2H); 6.47 (s, 1H); 6.95 (s, 2H); 7.10–7.37 (m, 6H); 7.85 (s, 1H); 7.87–7.93 (m, 2H); 9.12 (d, 1H, J=6.8 Hz). Anal. calcd. for C$_{54}$H$_{67}$N$_2$Cl$_2$PRu: C, 68.48; H, 7.13; N, 2.96; Cl, 7.49. Found: C, 68.71; H, 7.11; N, 3.77; Cl, 7.37.

Example 3

(3S,6R,7S,8S)-3,7-bis-(tert-butyl-dimethyl-silanyloxy)-4,4,6,8-tetramethyl-5-oxo-dec-9-enoic acid (Z)-(S)-1-acetyl-4-methyl-hepta-3,6-dienyl ester To an ice cold solution of 238.0 mg (1.42 mmol) of (Z)-(S)-3-hydroxy-6-methyl-nona-5,8-dien-2-one (prepared in analogy to S. J. Danishefsky et al., *J. Am. Chem. Soc.* 2003, 125, 2899–2901; S. J. Danishefsky et al. and U.S. Patent Application Publication No: 2004/0053910 A1) in 10 ml dichloromethane, 188.8 mg (1.51 mmol) of 4-dimethylamino-pyridine and 296.0 mg (1.51 mmol) 1-(3-dimethylaminopropyl)-3-ethylcarbodiimide hydrochloride were added. Within 10 min, a solution of 473.0 mg (0.95 mmol) of (3S,6R,7S,8S)-3,7-bis-(tert-butyl-dimethyl-silanyloxy)-4,4,4,6,8-tetramethyl-5-oxo-dec-9-enoic acid (prepared in analogy to S. J. Danishefsky et al., *J. Am. Chem. Soc.* 2003, 125, 2899–2901; S. J. Danishefsky et al., U.S. 2004/0053910 A1) in 10 ml dichloromethane was added and the resulting pink solution stirred at r.t. for 16 h. The reaction mixture was evaporated to dryness and the resulting crude product purified by silica gel chromatography (hexane/ethylacetate 4:1) to yield 574.0 mg (93%) of the title compound with 99.5% purity (HPLC method: Chirobiotic V column, 4.6×250 mm, solvent A: n-hexane, B: ethanol, gradient from A/B 95/5 to 50/50 within 5 min and 4 min at 50/50, flow 0.5 ml/min, 18° C., 210 nm. Retention time: 5.8 min) as a colorless oil. MS: 668.6 (M+NH$_4^+$). $^1$H-NMR (300 MHz, CDCl$_3$): –0.06 (s, 3H); 0.00 (s, 6H); 0.02 (s, 3H); 0.79 (s, 9H); 0.85 (s, 9H); 0.95 (d, 3H, J=4.5 Hz); 0.97 (d, 3H, J=4.5 Hz); 1.03 (s, 3H); 1.14 (s, 3H); 1.62 (d, 3H, J=0.8 Hz); 1.95–2.15 (m, 1H); 2.07 (s, 3H); 2.30 (dd, 1H, J=17.0, 6.4 Hz); 2.40 (t, 2H, J=6.4 Hz); 2.52 (dd, 1H, J=17.0, 3.2 Hz); 2.60–2.75 (m, 2H); 2.99 (quint., 1H, J=7.0 Hz); 3.77 (dd, 1H, 7.2, 2.1 Hz); 4.30 (dd, 1H, J=6.4, 3.4 Hz); 4.85–5.05 (m, 5H); 5.12 (t, 1H, J=7.2 Hz); 5.55–5.75 (m, 1H); 5.85 (ddd, 1H, J=17.2, 10.6, 7.7 Hz). Anal. calcd. for C$_{36}$H$_{66}$O$_6$Si$_2$: C, 66.41; H, 10.27. Found: C, 66.27; H, 10.27.

Example 4

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione A solution of 0.50 g (0.77 mmol) of (3S,6R,7S,8S)-3,7-bis-(tert-butyl-dimethyl-silanyloxy)-4,4,6,8-tetramethyl-5-oxo-dec-9-enoic acid (Z)-(S)-1-acetyl-4-methyl-hepta-3,6-dienyl ester in 1.9 l toluene was heated at reflux. A solution of 97.8 mg (0.12 mmol) of [RuCl$_2$(PCy$_3$)(ImH$_2$Mes)(benzylidene)] (Grubbs 2$^{nd}$ generation RCM catalyst, commercially available from Sigma-Aldrich Corp. St. Louis, Mo. 63103) in 100 ml toluene was added and the resulting yellow solution stirred for 30 min at reflux. 18.06 mg (0.12 mmol) 2-mercaptonicotinic acid was added, and after 5 min the hot reaction solution was filtered over a silica gel pad. The filtrate was evaporated to dryness. To remove residual toluene, the crude product was dissolved in 60 ml ethanol and the formed solution evaporated to dryness to yield 409.0 mg of crude product with 59% purity (HPLC method: Chirobiotic V column, 4.6×250 mm, solvent A: n-hexane, B: ethanol, gradient from A/B 95/5 to 50/50 within 5 min and 4 min at 50/50, flow 0.5 ml/min, 18° C., 210 nm. Retention times: Starting material 5.8 min, product 6.6 min). Silica gel chromatographic purification of the crude product (hexane/ethylacetate 9:1) yielded 231.5 mg (combined fractions) of the title compound as an off-white solid with 93% purity (45% yield). M.p.: 85° C. MS: 622.4 (M$^+$). $^1$H-NMR (300 MHz, CDCl$_3$): –0.15 (s, 3H); –0.10 (s, 3H); –0.03 (s, 3H); 0.00 (s, 3H); 0.75 (s, 9H); 0.83 (s, 9H); 0.93 (d, 3H, J=7.0 Hz); 1.01 (s, 3H); 1.02 (d, 3H, J=7 Hz); 1.08 (s, 3H); 1.58 (s, 3H); 2.12 (s, 3H); 2.15–2.85 (m, 2H); 2.87–2.53 (m, 2H); 2.62 (dd, 1H, J=15.5, 2.6 Hz); 2.84 (dd, 2H, J=15.5, 8.0 Hz); 2.97 (dd, 1H, J=15.1, 4.8 Hz); 3.84 (d, 1H, J=8.6 Hz); 4.11 (dd, 1H, J=8.6, 2.4 Hz); 489 (dd, 1H, J=8.5, 2.5 Hz); 5.06 (t, 1H, J=7.5 Hz); 5.20–5.30 (m, 1H); 5.52 (dd, 1H, J=16.1, 8.5 Hz). Anal. calcd. for C$_{34}$H$_{62}$O$_6$Si$_2$: C, 65.55; H, 10.03; Si, 9.02. Found: C, 64.76; H, 9.84; Si, 8.96.

Example 5

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione In an analogous manner to Example 4 but in the presence of [RuCl$_2$(PCy$_3$)(ImMes)(3-phenyl-indenylidene)] (109.1 mg, 0.115 mmol) instead of [RuCl$_2$(PCy$_3$)(ImH$_2$Mes)(benzylidene)] as catalyst, 477.8 mg of crude product with 70% purity (HPLC method described in Example 4) was isolated. Silica gel chromatographic purification of the crude product (hexane/ethylacetate 9:1) yielded 287.2 mg (combined fractions) of the title compound with 95% purity (57% yield).

Example 6

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione A solution of 50.0 mg (76.8 μmol) of (3S,6R,7S,8S)-3,7-bis-(tert-butyl-dimethyl-silanyloxy)-4,4,6,8-tetramethyl-5-oxo-dec-9-enoic acid (Z)-(S)-1-acetyl-4-methyl-hepta-3,6-dienyl ester in 200 ml toluene was heated at reflux. 10.8 mg (11.5 μmol) of [RuCl$_2$(PCy$_3$)(ImH$_2$Mes)(3-phenyl-indenylidene)] was added and the resulting yellowish solution stirred at reflux. After 30 min, a 50 ml sample was evaporated to dryness and to remove residual toluene, redissolved in 25 ml ethanol and evaporated to dryness to yield the title compound with 80% purity (HPLC method described in Example 4).

Example 7

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione In an analogous manner to Example 6 but in the presence of 3.3 mg (3.8 μmol) of [RuCl$_2$(PCy$_3$)(ImH$_2$Mes)(benzylidene)] instead of [RuCl$_2$(PCy$_3$)(ImH$_2$Mes)(3-phenyl-indenylidene)] as catalyst, the title compound was isolated with 67% purity (HPLC method described in Example 4).

Example 8

(10E,13Z)-(4S,7R,8S,9S,16S)-1 6-Acetyl-4,8-bis-(tert-butyl-dimethyl-silanyloxy)-5,5,7,9,13-pentamethyl-oxacyclohexadeca-10,13-diene-2,6-dione In an analogous manner to Example 6 but in the presence of 3.6 mg (3.8 μmol) of [RuCl$_2$(PCy$_3$)(ImMes)(3-phenyl-indenylidene)] instead of [RuCl$_2$(PCy$_3$)(ImH$_2$Mes)(3-phenyl-indenylidene)] as catalyst, the title compound was isolated with 83% purity (HPLC method described in Example 4).

Example 9

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione In an analogous manner to Example 6 but in the presence of 10.6 mg (11.5 μmol) of [RuCl$_2$(PCy$_3$)(ImH$_2$Pr)(benzylidene)] (prepared according to J. C. Mol, Adv. Synth. Catal. 2002, 344, 671–677) instead of [RuCl$_2$(PCy$_3$)(ImH$_2$Mes)(3-phenyl-indenylidene)] as catalyst, the title compound was isolated with 49% purity (HPLC method described in Example 4).

Example 10

(10E,13Z)-(4S,7R,8S,9S,16S)-16-Acetyl-4,8-bis-(tert-butyl-dimethyl-silanyloxy)-5,5,7,9,13-pentamethyl-oxacyclohexadeca-10,13-diene-2,6-dione In an analogous manner to Example 6 but in the presence of 10.7 mg (11.5 μmol) of [RuCl$_2$(PPh$_3$)(ImMes)(3-phenyl-indenylidene)] (prepared according to S. P. Nolan, *Organometallics* 1999, 18, 5416–5419) instead of [RuCl$_2$(PCy$_3$)(ImH$_2$Mes)(3-phenyl-indenylidene)] as catalyst, the title compound was isolated with 59% purity (HPLC method described in Example 4).

Unless stated to the contrary, all compounds in the examples were prepared and characterized as described. All ranges recited herein encompass all combinations and sub-combinations included within that range limit. All patents and publications cited herein are hereby incorporated by reference in their entirety for any purpose.

What is claimed is:

1. A process for the preparation of an epothilone derivative of formula I:

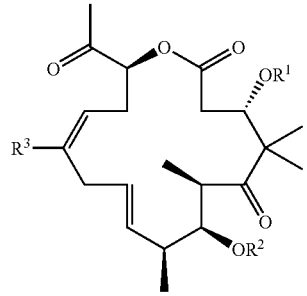

wherein:
R$^1$ is hydrogen or a protecting group;
R$^2$ is hydrogen or a protecting group; and
R$^3$ is methyl or trifluoromethyl;

comprising reacting an olefin-precursor compound of formula II:

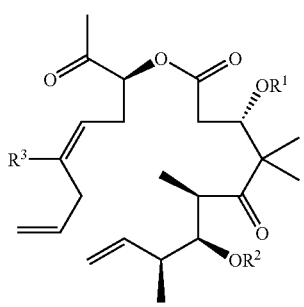

wherein:
R¹ is hydrogen or a protecting group;
R² is hydrogen or a protecting group; and
R³ is methyl or trifluoromethyl;
in the presence of an organic solvent and a Ruthenium catalyst of formula III:

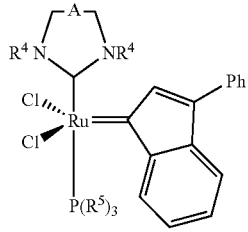

wherein:
A is a single or a double bond,
R⁴ is 2,4,6-trimethylphenyl; and
R⁵ is cyclohexyl.

2. The process according to claim 1, wherein R³ is methyl.

3. The process according to claim 1, wherein A is a double bond and R⁵ is cyclohexyl.

4. The process according to claim 1, wherein A is a single bond R⁵ is cyclohexyl.

5. The process according to claim 1, wherein the organic solvent is selected from the group consisting of toluene, methylene chloride, benzene and mesitylene.

6. The process according to claim 1, wherein the reaction temperature ranges from 20° C. to 165° C.

7. The process according to claim 1, wherein the amount of catalyst ranges from 0.1 to 15 mol % relative to the substrate.

* * * * *